(12) United States Patent
Corver et al.

(10) Patent No.: US 7,199,581 B2
(45) Date of Patent: Apr. 3, 2007

(54) MAGNETIC RESONANCE MEASURING SYSTEM DETERMINING THE MASS OF SAMPLES IN A PRODUCTION LINE WITH MONITORED DRIFT COMPENSATION

(75) Inventors: Jozef A. W. M. Corver, Nuenen (NL); Paulus C. J. M. Hendrickx, Baarle-Nassau (NL); Paul Stewart, Youngstown, NY (US); Ad van den Elshout, Dongen (NL); James M McKendry, Headington (GB); Malcolm Buckingham, Witney (GB); Graham Craigie, Wheatley (GB)

(73) Assignee: The BOC Group, Inc., Murray Hill, NJ (US)

( * ) Notice: Subject to any disclaimer, the term of this patent is extended or adjusted under 35 U.S.C. 154(b) by 173 days.

(21) Appl. No.: 10/836,786

(22) Filed: Apr. 30, 2004

(65) Prior Publication Data

US 2005/0116712 A1 Jun. 2, 2005

Related U.S. Application Data

(60) Provisional application No. 60/471,231, filed on May 16, 2003.

(51) Int. Cl.
*G01V 3/00* (2006.01)
(52) U.S. Cl. .................... 324/308; 324/307; 324/309
(58) Field of Classification Search ............... None
See application file for complete search history.

(56) References Cited

U.S. PATENT DOCUMENTS

| | | | |
|---|---|---|---|
| 3,796,873 A | 3/1974 | Ledgett | |
| 4,584,548 A * | 4/1986 | Inoue et al. | 335/299 |
| 4,727,325 A | 2/1988 | Matsui et al. | |
| 5,015,954 A | 5/1991 | Dechene et al. | |

(Continued)

FOREIGN PATENT DOCUMENTS

DE 1803372 A1 5/1970

(Continued)

OTHER PUBLICATIONS

Derwent WPI Abstract, UNILEVER NV, Package Weight Measuring System, NL 154001B, Jul. 15, 1977 (Corresponds to DE 1803372A1).

*Primary Examiner*—Diego Gutierrez
*Assistant Examiner*—Tiffany A. Fetzner
(74) *Attorney, Agent, or Firm*—Bernard Lau; Ira L. Zebrak

(57) ABSTRACT

Magnetic resonance measurement methods for determining the mass of samples are provided in which magnetic field homogeneity is determined, compensation is provided for potential drifts in the measuring system, and the presence of metal in samples is determined. The methods include applying a magnetic field in a first direction in an interrogation zone for creating a net magnetisation within a sample located within the interrogation zone; applying an alternating magnetic field in a second direction in the interrogation zone for temporarily changing the net magnetisation of the sample located within the interrogation zone; monitoring energy emitted by the sample as the net magnetisation of the sample returns to its original state and generating an output signal having a characteristic which is proportional to the energy emitted; and comparing the output signal of the monitoring with other data.

7 Claims, 8 Drawing Sheets

U.S. PATENT DOCUMENTS

| | | |
|---|---|---|
| 5,049,819 A | 9/1991 | Dechene et al. |
| 5,291,422 A | 3/1994 | Esztergar |
| 5,302,896 A * | 4/1994 | Dechene et al. ............ 324/307 |
| 5,343,150 A * | 8/1994 | Nakahata et al. ........... 324/316 |
| 5,530,350 A * | 6/1996 | Dechene et al. ............ 324/306 |
| 5,600,303 A * | 2/1997 | Husseiny et al. ........ 340/568.1 |
| 5,692,029 A * | 11/1997 | Husseiny et al. ............. 378/88 |
| 6,028,428 A | 2/2000 | Cunningham et al. |
| 6,246,231 B1 * | 6/2001 | Ashe ..................... 324/207.17 |
| 6,333,629 B1 * | 12/2001 | Pykett et al. ................ 324/307 |
| 6,362,619 B2 | 3/2002 | Prammer et al. |
| 6,377,049 B1 | 4/2002 | Benz et al. |
| 6,426,058 B1 | 7/2002 | Pines et al. |
| 6,528,991 B2 * | 3/2003 | Ashe ..................... 324/207.17 |
| 6,759,601 B1 * | 7/2004 | Petty et al. .................... 177/1 |
| 7,002,346 B2 * | 2/2006 | Schaepman et al. ........ 324/315 |
| 7,015,693 B2 * | 3/2006 | Corver et al. ............... 324/300 |
| 2003/0011359 A1 * | 1/2003 | Ashe ..................... 324/207.17 |
| 2005/0116712 A1 * | 6/2005 | Corver et al. ............... 324/309 |
| 2005/0122104 A1 * | 6/2005 | Corver et al. ............... 324/309 |
| 2005/0242808 A1 * | 11/2005 | McKendry et al. ......... 324/307 |
| 2005/0242809 A1 * | 11/2005 | McKendry et al. ......... 324/308 |
| 2005/0242811 A1 * | 11/2005 | Schaepman et al. ........ 324/315 |
| 2005/0242813 A1 * | 11/2005 | Aptaker et al. ............. 324/318 |
| 2005/0247493 A1 * | 11/2005 | Aptaker et al. ................. 177/1 |

FOREIGN PATENT DOCUMENTS

| | | |
|---|---|---|
| GB | 2149509 A | 6/1985 |
| WO | WO 99/67606 A1 | 12/1999 |

* cited by examiner

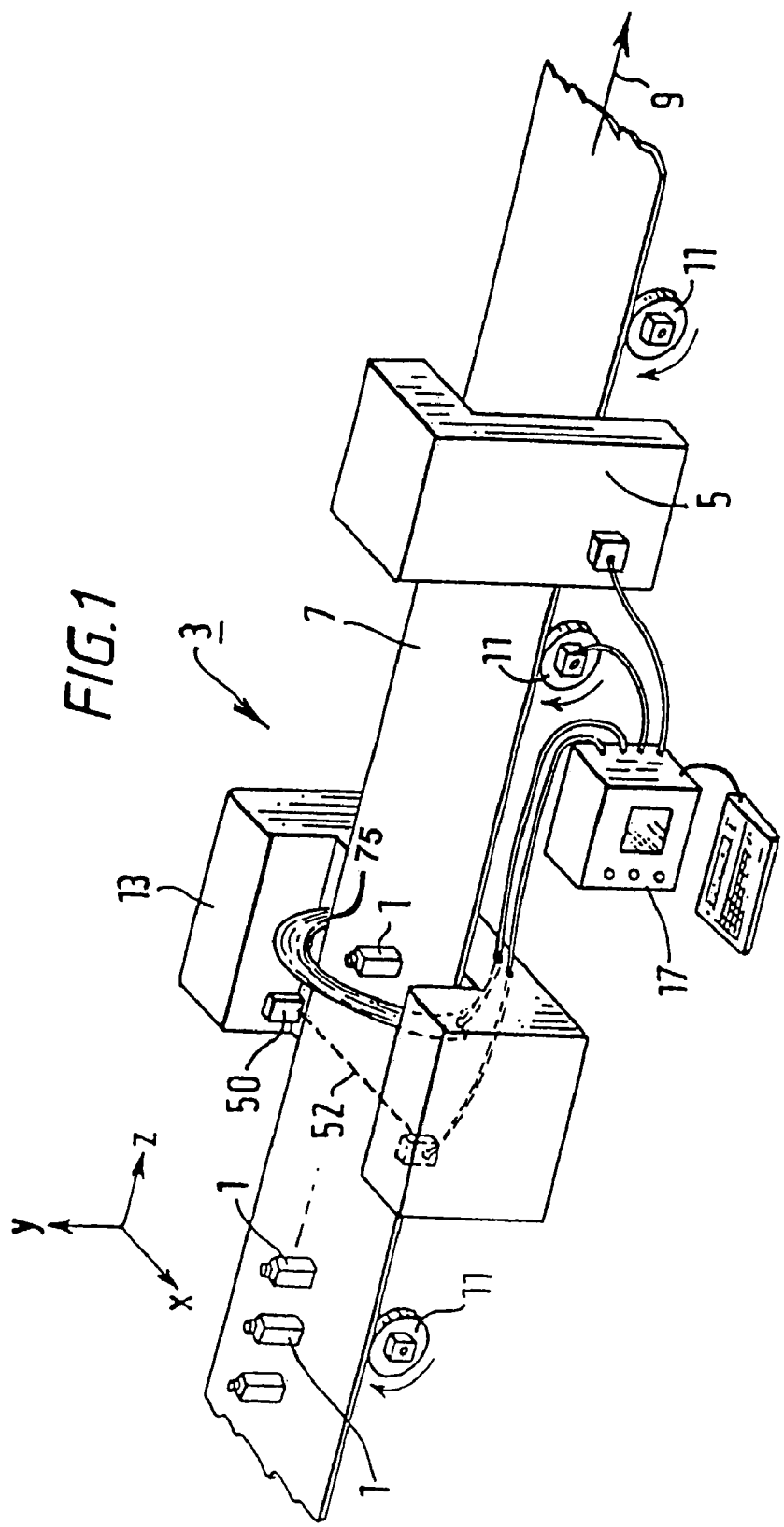

Prior Art

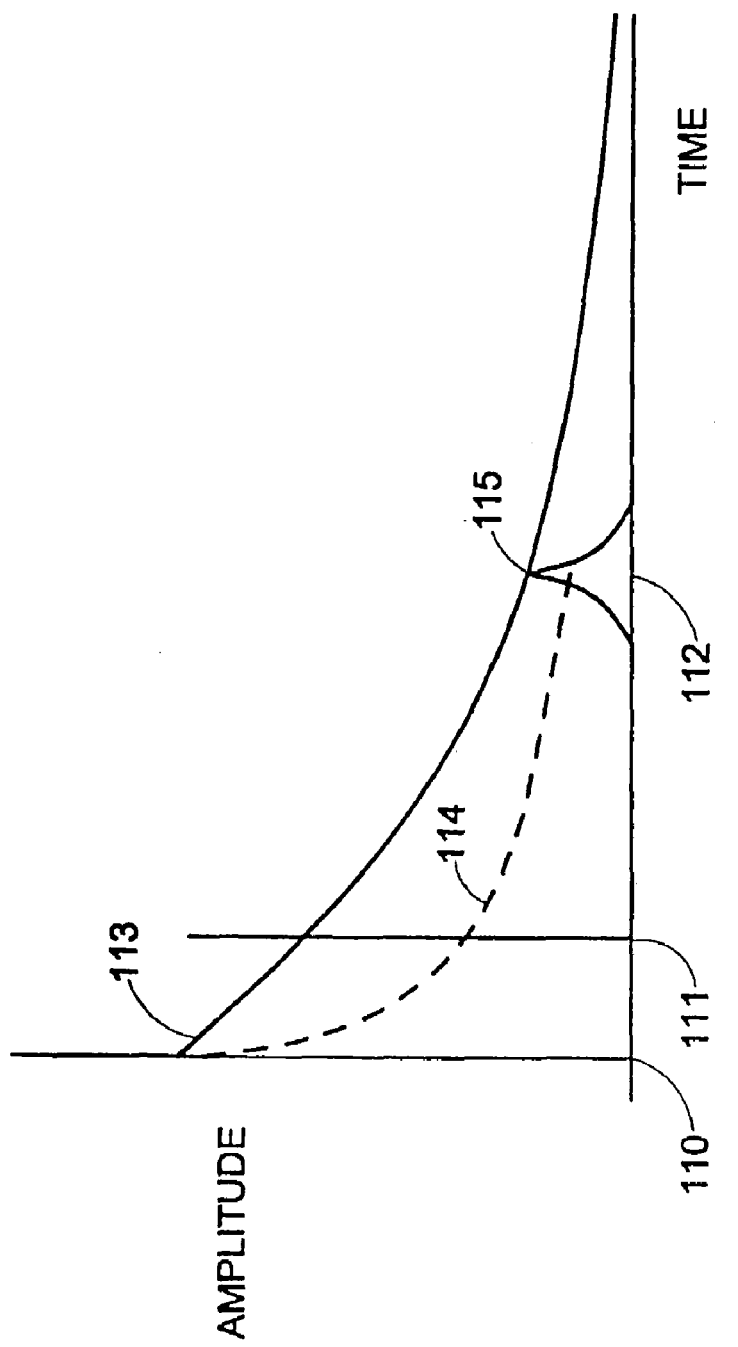

MAGNETIC RESONANCE MEASURING SYSTEM DETERMINING THE MASS OF SAMPLES IN A PRODUCTION LINE WITH MONITORED DRIFT COMPENSATION

CROSS REFERENCE TO RELATED APPLICATIONS

This application claims the benefit of the filing date of U.S. Provisional Application Ser. No. 60/471,231, filed May 16, 2003, which is incorporated herein by reference.

FIELD OF THE INVENTION

The invention relates to non-contact check weighing of samples using NMR techniques.

BACKGROUND

The nuclei of atoms that have a magnetic moment will have sharply defined frequencies of nuclear oscillation in a strong magnetic field (Larmor frequency). The frequency of oscillation of each atomic nucleus will depend on its mass, its dipole moment, the chemical bonding of the atom, the atom's environment (which will be affected by electromagnetic coupling to other atoms in the vicinity), and the strength of the magnetic field seen by the atom. Thus, the frequency of oscillation will be characteristic, not only of the various atomic species, but also of their molecular environments. By resonantly exciting these oscillations, the atomic species and their environments can be determined with accuracy. This phenomenon is known as "nuclear magnetic resonance," or NMR.

If a pulse of RF energy is applied at a resonance frequency of atoms of a particular species and environment (e.g. hydrogen atoms in a water environment), the atomic nuclei of this type and environment will resonantly be excited, and will later make a transition back to a low state of excitation. This transition is accompanied by emission of a radio-frequency signal, at the excitation frequency or a known lower frequency. The signal is known as the Free Induction Decay (FID) The amplitude and the shape of this FID-curve is related to the amount of nuclei involved in the process and to specific conditions and properties of the atoms in relation to the environment.

The use of NMR techniques in measurement, detection and imaging has become desirable in many scientific fields of endeavor. The non-invasive, non-destructive nature of NMR has facilitated application to industrial instrumentation, analysis and control tasks.

Almost every element in the periodic table has an isotope with a non-zero nuclear spin. This spin causes the nuclei to be magnetically active. Among magnetically active nuclei, NMR can only be performed on isotopes whose natural abundance is high enough to be detected. Commonly encountered magnetically active nuclei are $^1H$, $^{13}C$, $^{19}F$, $^{23}Na$, and $^{31}P$. The most common is $^1H$, which also possesses the largest magnetic moment, rendering it most advantageous for the performance of NMR spectroscopy.

Upon application to a sample of a static magnetic field, $B_o$, sample nuclear spins align with the field, parallel to the direction of the field. The magnetic moments can align themselves either parallel (NSNS) or antiparallel (NNSS) to the static field. Alignment parallel to the static field is the lower energy state and alignment against the field is the higher energy state. At room temperature, the number of nuclei having spins in the lower energy level, $N^+$, slightly outnumbers the number in the upper level, $N^-$. Boltzmann statistics provides that $$N^-/N^+ = \exp(-E/kT), \qquad (1)$$

where E is the energy difference between the spin states; k is Boltzmann's constant, $1.3805 \times 10^{-23}$ J/Kelvin; and T is the temperature in Kelvin. As the temperature decreases, so does the ratio $N^-/N^+$. As the temperature increases, the ratio approaches unity.

Owing to the slight imbalance of nuclei having spins at the higher state, a sample in a static magnetic field will exhibit a magnetization parallel to the static field. Magnetization results from nuclear precession (relaxation) around the static magnetic field. The frequency of this precession depends on the strength of the static magnetic field, and is defined as:

$$v = \gamma B, \qquad (2)$$

where B is the magnetic field strength and Gamma is the gyromagnetic ratio of at least one atom, typically hydrogen, in the sample material. The gyromagnetic ratio is related to the magnetic moment of the nucleus under analysis. The gyromagnetic ratio of protons is 42.57 MHz/Tesla. The frequency thus measured is known as the Larmor frequency, v, which can be conceptualized as the rate of precession of the nucleus in the static magnetic field or the frequency corresponding to the energy at which a transition between the upper and lower states can take place.

The fundamental NMR signal is derived by inducing transitions between these different alignments. Such transitions can be induced by exposing a sample to the magnetic component of an RF (radio frequency) signal, typically generated by an RF coil. When the magnetic component is applied perpendicularly to the magnetic field a resonance occurs at a particular RF frequency (identical to the precession frequency, the Larmor frequency), corresponding to the energy emitted or absorbed during a transition between the different alignments. When a strong magnetic field, such as in the range of 0.1–2 Tesla (1 T=10,000 Gauss) is used, this resonance typically occurs in the megahertz frequency range, corresponding to FM radio. Hence the radiation is known as Radio Frequency (RF) radiation.

The signal in NMR spectroscopy results from the difference between the energy absorbed by the spins which make a transition from the lower energy state to the higher energy state, and the energy emitted by the spins which simultaneously make a transition from the higher energy state to the lower energy state. The signal is thus proportional to the population difference between the states. NMR spectroscopy gains its high level of sensitivity since it is capable of detecting these very small population differences. It is the resonance, or exchange of energy at a specific frequency between the spins and the spectrometer, which gives NMR its sensitivity.

Pulsed NMR spectroscopy is a technique involving a magnetic burst or pulse, which is designed to excite the nuclei of a particular nuclear species of a sample being measured after the protons of such sample have first been brought into phase in an essentially static magnetic field; in other words the precession is modified by the pulse. Typically, the direction of the static magnetic field, $B_o$, is thought of as being along the Z-axis in three-dimensional space. At equilibrium, the net magnetization vector lies along the direction of the applied magnetic field $B_o$ and is called the equilibrium magnetization $M_o$. In this configuration, the Z component of magnetization $M_Z$ equals $M_o$. $M_Z$ is referred to as the longitudinal magnetization. There is no transverse ($M_X$ or $M_Y$) magnetization in such a case.

It is possible to change the net magnetization by exposing the nuclear spin system to energy of a frequency equal to the energy difference between the spin states. If enough energy is put into the system, it is possible to saturate the spin system and make $M_Z$=0. The time constant, which describes how $M_Z$ returns to its equilibrium value, is called the spin lattice relaxation time ($T_1$). The equation governing this behavior as a function of the time t after its displacement is:

$$M_Z = M_0(1-e^{-t/T1}) \qquad (3)$$

$T_1$ is therefore defined as the time required to change the Z component of magnetization by a factor of e. Hence, at $t=T_1$, $M_Z$=0.63 $M_0$. In order to properly perform repeated measurements, which is necessary in order to reduce background noise and enhance signal quality, $M_0$ should be allowed to return to $M_Z$. In other words, the longitudinal magnetization $M_Z$, which equals zero upon saturation, should be allowed to fully return to the +Z direction and attain its equilibrium value of $M_0$. While this theoretically would take forever, (i.e., following saturation, $M_Z=M_0$ when $t=\infty$), it is generally considered sufficient when $M_Z$=0.99 $M_0$, which occurs when $t=5T_1$. This places time constraints on the speed at which a sample may be measured multiple times or the overall throughput of samples through an interrogation zone.

If the spin system is oversaturated, forcing the net magnetization into the –Z direction, it will gradually return to its equilibrium position along the +Z axis at a rate also governed by $T_1$. The equation governing this behavior as a function of the time t after its displacement is:

$$M_z = M_o(1-2e^{-t/T1}) \qquad (4)$$

The spin-lattice relaxation time ($T_1$) is the time to reduce the difference between the longitudinal magnetization ($M_Z$) and its equilibrium value by a factor of e. Here, too, an elapsed time of $t=5\ T_1$ is required in order for $M_Z$ to return to a value of 0.99 $M_O$, placing a similar time constraint on sample throughput.

If the net magnetization is rotated into the XY plane by a 90° pulse, it will rotate about the Z-axis at a frequency equal to the frequency of a photon, having the energy corresponding to a transition between the two energy levels of the spin. This frequency is called the Larmor frequency. In addition to the rotation, the net magnetization, now in the XY plane, starts to dephase because each of the spin packets making it up is experiencing a slightly different magnetic field and hence rotates at its own Larmor frequency. The longer the elapsed time, following the pulse, the greater the phase difference. If the detector coil is sensitive to measurements of fields in the X direction alone, the dephasing results in a decaying signal, eventually approaching zero. The time constant, which describes this decay of the transverse magnetization, $M_{XY}$, is called the spin-spin relaxation time, $T_2$.

$$M_{XY} = M_{XY0}\, e^{-t/T2} \qquad (5)$$

$T_2$ is always less than or equal to $T_1$. The net magnetization in the XY plane goes to zero while the longitudinal magnetization grows until $M_0$ returns to the +Z direction. Any transverse magnetization behaves the same way.

The spin-spin relaxation time, $T_2$, is the time to reduce the transverse magnetization by a factor of e. The difference between spin-lattice relaxation and spin-spin relaxation is that the former works to return $M_z$ to $M_0$, while the latter works to return $M_{xy}$ to zero. $T_1$ and $T_2$ were discussed separately above, for clarity. That is, the magnetization vectors are considered to fill the XY plane completely before growing back up along the Z-axis. Actually, both processes occur simultaneously, with the only restriction being that $T_2$ is less than or equal to $T_1$.

Two factors contribute to the decay of transverse magnetization—(1) molecular interactions (said to lead to a pure $T_2$ molecular effect), and (2) variations in $B_o$ (the applied static field), said to lead to an inhomogeneous $T_2$ effect. The combination of these two factors is what actually results in the decay of transverse magnetization. The combined time constant is called "$T_2$ star" and is given the symbol $T_2^*$. The relationship between the $T_2$ from molecular processes and that from inhomogeneities in the magnetic field is $$1/T_2^* = 1/T_2 + 1/T_{2inh}. \qquad (6)$$

The source of the inhomogeneities can be natural fluctuations in a field, or imperfections in the magnets generating the field or magnetic contaminants, such as iron or other ferromagnetic metals.

In practice, to actually measure a sample using NMR, a sample is first placed in a static magnetic field, $B_o$, which is the interrogation zone of the instrument. Next, a magnetic pulse is applied, which rotates the magnetization vector to a desired extent, typically 90° or 180°. A 90° pulse, for example, rotates the magnetization vector from the Z-direction into the XY plane resulting in transverse magnetization, $M_{XY}$, as discussed above. After the application of the pulse, there occurs a free induction decay (FID) of the magnetization associated with the excited nuclei.

Traditional Fourier Transform analysis transforms a time domain spectrum (amplitude of magnetization vectors vs. time) into a frequency domain spectrum (frequency vs. relative amplitude), which separates individual frequencies out of a multiphase spectrum. This separation can be used to advantage in studying the nuclei of interest. The duration of the pulses, the time between the pulses, the pulse phase angle and the composition of the sample are parameters, which affect the sensitivity of this technique.

International Patent Application No. WO9967606, incorporated herein by reference as if fully written out below, describes a check weighing system for samples on a production line, including a magnet for creating a static magnetic field over an interrogation zone to create a net magnetization within a sample located within the interrogation zone, and an RF coil for applying an alternating magnetic field over the interrogation zone to cause excitation of the sample according to the principles of NMR.

The use of NMR for techniques for check weighing samples on a production line encounters a variety of difficulties, including but not limited to the presence of interfering species such as metal particles either within the sample container or elsewhere in the system, effects of temperature on the magnet or electronics, humidity in the sample or system, and mechanical instability of the containers.

It would be desirable to provide a system and method for identifying and/or compensating for the above noted potential sources of imprecise measurements for an NMR sample check weighing system.

SUMMARY

The present methods relate to check weighing material contained in a container, which is passing along a product filling line, i.e. production line, by nuclear magnetic resonance (NMR) techniques.

The presence of ferrous particles in the measurement volume creates significant degradation of the accuracy of the measurement. A continuous, on-line method is provided to determine the presence and impact of these particles. This can be used as an indicator for cleaning activities needed.

It is highly important for the functionality of TL light sources, to contain a limited amount of mercury. Heretofore it has not been possible to determine the presence of this metal in a non-destructive way.

There are a vast number of products of which the quality depends on the total absence of metallic particles. NMR is highly sensitive to the presence of metallic particles in its measuring volume, and can therefore be applied to their detection.

An improvement is provided in a magnetic resonance method for determining the mass of samples in a production line, comprising:

applying a first magnetic field in a first direction in an interrogation zone for creating a net magnetisation within a sample located within the interrogation zone;

applying an alternating magnetic field in a second different direction in the interrogation zone for temporarily changing the net magnetisation of the sample located within the interrogation zone;

monitoring energy emitted by the sample as the net magnetisation of the sample returns to its original state and generating an output signal having a characteristic which is proportional to the energy emitted;

comparing the output signal characteristic with like data obtained from at least one similar sample of known mass; and determining the mass of the sample;

characterised by:

applying a 90° excitation RF spin pulse to the sample;

monitoring the free induction decay energy of the sample and generating and measuring the characteristic of the spin output signal corresponding thereto;

applying a 180° excitation RF echo pulse to the sample;

monitoring the echo-induced energy emitted and generating and measuring the characteristic of the echo output signal corresponding thereto; and comparing the mathematical relationship between the characteristic of the spin output signal and the characteristic of the echo output signal.

The comparison of the spin signal and echo signal can comprise calculating the ratio between the spin signal and echo signal, or any other suitable mathematical technique such as integration.

Further, an improvement is provided in a magnetic resonance method for determining the mass of samples, providing compensation of drift in the magnetic resonance measuring system, comprising:

a) applying a first magnetic field in a first direction in an interrogation zone for creating a net magnetization within the sample located within the interrogation zone;

b) applying an alternating magnetic field in a second direction in the interrogation zone for temporarily changing the net magnetization of the sample located within the interrogation zone;

c) monitoring energy emitted by the sample as the net magnetization of the sample returns to its original state and generating an output signal having a characteristic which is proportional to the energy emitted; and d) comparing the output signal characteristic with like data obtained from at least one similar sample of known mass; and e) determining the mass of the sample;

characterized by:

maintaining a constant stability sample within access of the interrogation zone during measurement of the samples;

at least periodically determining the mass of the constant stability sample by steps a) through c);

comparing the constant stability sample mass measurements to determine, over time, the amount of the drift in the magnetic resonance measuring system; and, when appropriate adjusting sample mass measurement values to compensate for the amount of drift in the magnetic resonance measuring system.

A method of determining the presence of metal in samples is provided comprising:

maintaining a constant stability sample within an interrogation zone during testing of the samples;

applying a first magnetic field in a first direction in an interrogation zone for creating a net magnetisation within the constant stability sample and the samples located within the interrogation zone;

applying an alternating magnetic field in a second direction in the interrogation zone for temporarily changing the net magnetisation of the constant stability sample and the samples located within the interrogation zone;

monitoring energy emitted by the constant stability sample and the samples as the net magnetisation of the constant stability sample and the samples returns to its original state and generating an output signal having a characteristic which is proportional to the energy emitted; and comparing the output signal characteristic of the constant stability sample and any of the samples, with the stable output signal characteristic of the constant stability sample in the absence of the samples, to identify distortion of the stable signal amplitude indicating the presence of metal in the samples.

A method of determining the presence of metal in samples is provided comprising:

applying a first magnetic field in a first direction in an interrogation zone for creating a net magnetisation within the samples located within the interrogation zone;

applying an alternating magnetic field in a second direction in the interrogation zone for temporarily changing the net magnetisation of the samples located within the interrogation zone;

monitoring energy emitted by the samples as the net magnetisation of the constant stability sample and the samples returns to its original state and generating an output signal having a characteristic which is proportional to the energy emitted; and comparing the output signal characteristic generated by said monitoring with like data obtained from at least one similar sample having no metal content, to identify distortion from the corresponding similar sample signal characteristic indicating the presence of metal in the samples.

The comparison with like data may relate the signal amplitude of the at least one similar sample to the corresponding output signal amplitude generated by said monitoring step.

BRIEF DESCRIPTION OF THE DRAWINGS

FIG. 1 is a schematic view of a production line with an NMR check weighing station for checking that each container passing through the weighing station has the desired amount of product.

FIG. 3 is a graph demonstrating the use of spin-echo techniques to indicate the effect of ferrous particles in the system on the NMR sample measurement.

DETAILED DESCRIPTION

Figure 1A:
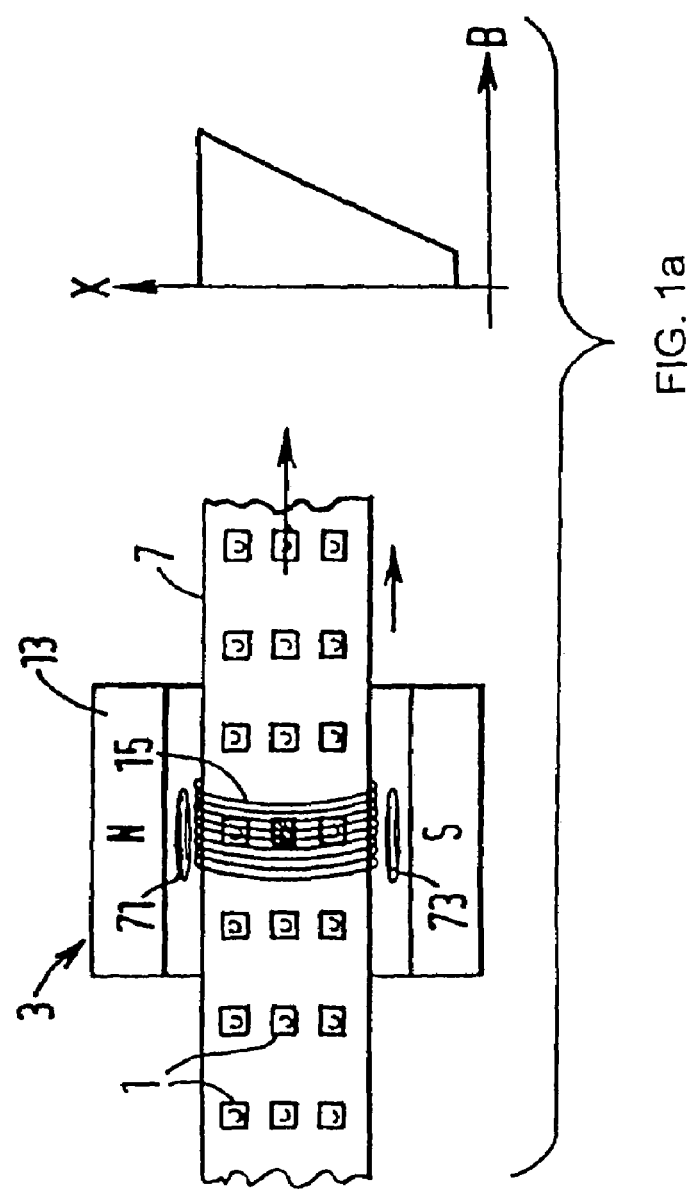
FIG. 1a diagrammatically illustrates the form of a check weighing station according to an alternative embodiment in which a magnetic field gradient is applied over an interrogation zone.

The present methods relate to check weighing material contained in a container, which is passing along a production line, by nuclear magnetic resonance (NMR) techniques. As one example, check weighing is used by the pharmaceuticals industry for the monitoring and regulation of the amount of a drug in a sealed glass vial during filling. The drug weight can be as small as a fraction of a gram, and is required to be weighed with an accuracy of a few percent or better, in a vial weighing tens of grams at a rate of several weighings per second. Conventionally, to obtain the required accuracy, it is necessary to remove the vials from the production line and to weigh them on precision balances both before and after filling in order to take into account the weight of the container. Because this is time-intensive, only a fraction of the product can be tested. If deviations from expected values are detected, a large batch of product can be wasted before the problem is identified. As the vial must be weighed both before and after filling, the weighing must be performed in an aseptic environment between filling and sealing.

An NMR apparatus for determining the mass of a sample generally may comprise means for generating a static magnetic field in a first direction through the sample; means for applying an alternating excitation magnetic field in a second different direction through the sample; means for sensing energy emitted by the sample in response to the excitation magnetic field and for outputting a signal in dependence thereon; and means for comparing the signal output by said sensing means with stored calibration data to provide an indication of the mass of the sample. Such an apparatus can be used on-line in a product filling line. It can provide a non-contacting measure of the mass of the contents of a container independently of the container mass, if the container is made of a material which is not responsive to NMR, and is useful for determining the mass of small quantities of sample such as samples weighing between 0.1 grams and 10 grams which may be contained in glass containers of 20 grams or more, providing an indication of mass and not weight of the sample.

The apparatus can be used to measure the contents of a container by filling the container with the predetermined amount of sample; transporting each of the filled containers to a weighing station; weighing the sample within each of the containers; sealing the sample within the container; and rejecting any containers which do not contain the predetermined amount of sample within a predetermined tolerance. The weighing of the sample includes generating a static magnetic field in a first direction in an interrogation zone for creating a net magnetization within a sample located within the interrogation zone; applying a pulse of alternating magnetic field in a second different direction in the interrogation zone for temporarily changing the net magnetization of the sample located within the interrogation zone; sensing energy emitted by the sample as the net magnetization of the sample returns to its original state and outputting a signal in dependence thereon; and comparing the signal output by the sensing step with calibration data which relates the mass of at least one similar sample of known mass to the corresponding signal output by the sensing step, to provide the indication of the mass of the sample within each container.

In addition to pharmaceuticals, such an apparatus and method can be used in a variety of applications, including but not limited to cosmetics, perfumes, industrial chemicals, biological samples and food products. It can measure high value products where 100% sampling can reduce wastage, and can be used to determine the mass of samples that are in solid form, in powder form, in liquid form and in gas form, or any combination thereof.

FIG. 1 shows a portion of a production line, which fills glass vials 1 with a drug sample. Included is a weighing station 3 that is provided "in-line" for weighing each of the filled non-continuous and discrete samples in vials that pass therethrough, and a reject station 5 that removes those vials from the line that do not have the sufficient amount of the drug to meet product specifications. The vials 1 are transported to the weighing station 3 from a filling (and optionally sealing) station (not shown) by a conveyor belt 7 which, as represented by the arrow 9, moves in the z direction through the action of rotating conveyor wheels 11. The weighing station uses NMR techniques of measurement to determine the mass of the drug sample within each of the glass vials 1. As those skilled in the art will appreciate, glass vials are useful as the container, because they do not give a signal that might interfere with the measurement process. In this embodiment, the weighing station 3 comprises a permanent magnet 13, an RF coil 15 and a computer control system 17. The magnet 13 is creates a homogeneous direct current (DC) or static magnetic field in the x direction across the conveyor belt 7. The sample in the glass vial contains nuclei which each possess a magnetic moment, e.g. 1H nuclei (protons). This magnetic moment, discussed above, is a result of the spin of the nuclei.

In most NMR systems, the static magnetic field strength is such that the Larmor frequency of the sample is in the radio frequency range of the electromagnetic spectrum. Applying an alternating current (AC) magnetic field to the sample at the sample's Larmor frequency and orientated orthogonal to the static magnetic field, will cause the sample's net magnetization to rotate about the AC magnetic field's axis, away from the direction of the static field. In this embodiment, this magnetic field is generated by applying a corresponding AC current to the RF coil 15. The angle of rotation of the net magnetization can be varied by varying the amount of energy delivered to the RF coil 15.

In this exemplified embodiment, an excitation field that causes a 90° rotation is used to excite the sample. After the 90° pulse has been applied to the sample, the sample is left in a high-energy, non-equilibrium state, from which it will relax back to its equilibrium state. As it relaxes, electromagnetic energy at the Larmor frequency is emitted, the magnetic component of which induces current in the RF coil 15, the peak amplitude of which varies with, among other things, the number of magnetic moments in the sample and hence the number of molecules in the sample. The received signal is then passed to the computer control system 17, which compares the peak amplitude of the signal received from the unknown sample, with the peak amplitude of a signal received from a calibration sample with a known mass (or weight), to determine the mass (or weight) of the sample being tested. The check weighing station 3 may be able to generate and receive signals at different Larmor frequencies needed to be able to excite different NMR responsive elements in samples. If the computer control system 17 can store calibration data for each of the different samples, then the check weighing station would be able to determine the mass of various samples using the NMR signals from the different NMR responsive elements.

The operation of one embodiment is described in detail with reference to FIG. 2, a block diagram of the principal components of the computer control system 17 of this embodiment. The control system comprises a connection terminal 21 for connecting the control system to the RF coil 15. The connection terminal 21 is connectable, through switch 23, to a signal generator 25 and a power amplifier 27 which are operable to generate and amplify respectively the excitation signal which is applied to the RF coil 15. The connection terminal 21 is also connectable, through the switch 23, to a receiving amplifier 31 which amplifies the signal received from the sample under test. This amplified signal is then filtered by the filter 33 to remove noise components and then passed to the mixer 35 where the received signal is down converted to an intermediate frequency (IF) by multiplying it with an appropriate mixing signal generated by the signal generator 25. The IF signal output by the mixer 35 is then filtered by the filter 37 to remove the unwanted components generated by the mixer 35. The filtered IF signal is then converted into a corresponding digital signal by the A/D converter 39 and is then passed to the microprocessor 41.

As shown by the dashed control lines 43 and 45, the microprocessor 41 controls the operation of the signal generator 25 and the switch 23. The microprocessor 41 may operate to ensure that the signal generator 25 generates the excitation signal when the filled vial 1 is at the desired location within the check weighing station 3. The microprocessor 41 knows when the vial 1 is at the correct location from a signal received from the position sensor electronics 47 which is connected, through connection terminal 49, to an optical position sensor 50 mounted in the check weighing station 3. Referring to FIG. 1, when the glass vial 1 passes by the optical position sensor 50, a light beam 52 is broken. This is detected by the position sensor electronics 47 which in turn signals the microprocessor 41. Based on this information and the speed of the conveyor belt 7 (provided by the conveyor controller 51), the microprocessor determines the appropriate timing for the application of the burst of excitation current and signals the signal generator 25 accordingly.

As those skilled in the art of magnetic resonance will appreciate, it takes a finite period of time after the sample enters the static field generated by the magnet 13 for the net magnetisation of the sample to develop along the X-direction. If the excitation signal is applied to the RF coil 15 before the magnetisation has fully developed, then the strength of the signal generated by the sample will not be at its maximum.

The net magnetisation and thus the strength of the resultant signal produced by a sample varies with time in the static magnetic field. The longitudinal relaxation time depends upon the sample being tested and the strength of the static magnetic field. Therefore, given the strength of the static magnetic field and the type of sample which is being tested, the relaxation time can be determined. This information, combined with the speed of the conveyor belt 7, determines the minimum length of the magnet 13 in the Z-direction which is required to ensure that as large a signal as possible is generated by the sample under test.

In one embodiment, a capacitor (not shown) is connected across the ends of the RF coil 15 so that it is tuned to the Larmor frequency of the sample. The Larmor frequency of an MR responsive element such as hydrogen is calculated by multiplying the static magnet's DC magnetic field strength by the gyromagnetic ratio for the element (which for hydrogen is 42.57 MHz/Tesla). The gyromagnetic ratio for other MR responsive elements can be found in CRC Handbook of Chemistry & Physics, published by CRC Press Inc. The Larmor frequency of an MR responsive element such as hydrogen is calculated by multiplying the static magnet's DC magnetic field strength by the gyromagnetic ratio for the element (which for hydrogen is 42.57 MHz/Tesla). The gyromagnetic ratio for other MR responsive elements can be found in CRC Handbook of Chemistry & Physics, published by CRC Press Inc. The tuning of the RF coil 15 in this way makes the system less susceptible to electromagnetic interference or to other MR signals from nuclei with different gyromagnetic ratios. The excitation current flowing through the RF coil 15 generates a corresponding magnetic field in the Z-direction. This excitation magnetic field causes the net magnetisation of the sample in the vial 1 to rotate or precess about the Z-axis at the Larmor frequency. When the excitation current is removed from the RF coil 15, the nuclei in the sample begin to relax back to their equilibrium positions, emitting RF energy at the Larmor frequency as they do so. This induces a signal in the RF coil 15 which is seen to decay exponentially and is referred to as the transverse relaxation time. This depends upon the sample being tested and not on the static field strength.

As shown, the peak amplitude of the induced signal is at its maximum shortly after the excitation current stops, after which point the signal decays to zero. The amplitude of the signal induced in the RF coil 15 by the sample is directly proportional to the number of magnetic moments in the sample. Consequently, in this embodiment, the microprocessor 41 monitors the peak signal level which it receives from the A/D converter 39 after the excitation signal has been removed from the RF coil 15. Alternatively the microprocessor can determine the average signal over a period of time or fit the shape of the curve in order to improve accuracy.

In one embodiment, the microprocessor 41 then compares this peak signal level with calibration data obtained by testing a similar sample or samples of known mass, to provide an indication of the mass of the sample currently being tested. In this embodiment, this calibration data is obtained from a number of similar samples of different known masses during a calibration routine before the production batch is begun and is stored in memory 53. In this embodiment, the calibration data is a function which relates the peak amplitude of the MR signal received from the sample under test to the mass of the sample.

As described in the embodiments above, the RF probe monitors the energy emitted by the sample as the net magnetisation of the sample returns to its original state of equilibrium, and generates an output signal having a characteristic that is proportional to the energy emitted, such as current amplitude. The computer control system receives the RF probe output signal. A processor compares the current amplitude or other output signal characteristic with corresponding data obtained from at least one similar sample of known mass, and determines the mass of the sample from die results of the comparison. It is to be understood that although for purposes of illustration the embodiment has been described as measuring the peak amplitude of the induced signal, any chemometric characterization technique can be used that derives a single value from the energy emitted and the output signal generated. In general, comparison techniques may include comparing the FID characteristics of the sample with like FID characteristics of at least one known sample, i.e., the calibration data.

In one embodiment, if the microprocessor 41 determines that the mass of the current sample being analysed is not of the required mass within a given tolerance, it outputs a control signal on control line 55 to the reject controller 57. The reject controller then outputs a signal to output terminal 59 which is connected to the reject station 5, for causing the reject station to remove the current vial 1 being tested from the conveyor belt 7 when it arrives at the reject station 5.

Figure 2:
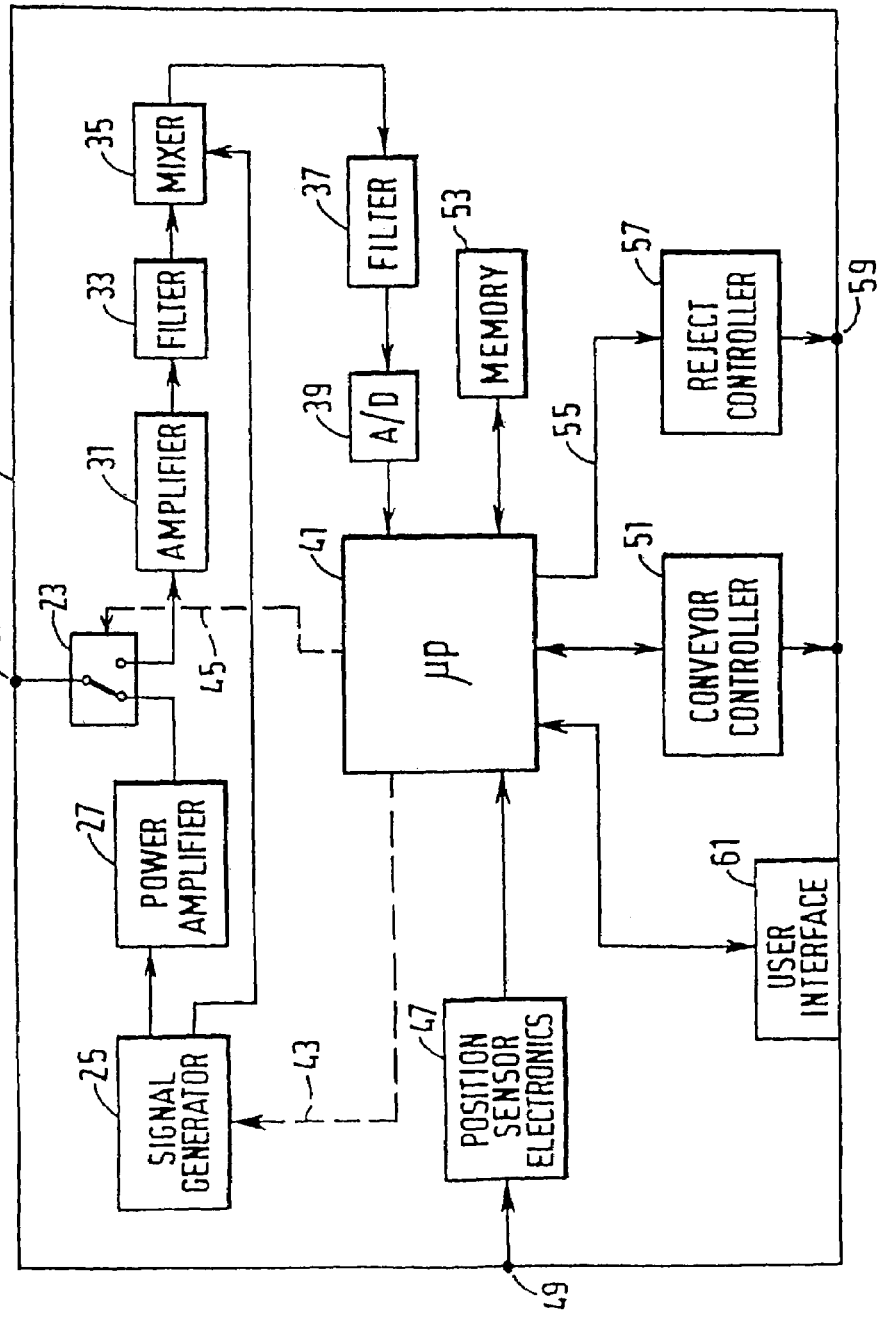
FIG. 2 is a block diagram of excitation and processing electronics that form part of and control the check weighing station shown in FIG. 1.

As shown in FIG. 2, the computer control system 17 may also comprise a user interface 61 for allowing the user to program into the control system 17 what the correct mass of each sample should be for a given batch of product.

In certain embodiments, a single measurement of a sample's mass is determined for each vial. The accuracy of the measurement can be improved by taking an average of repeated measurements. However, the rate at which measurements can be made on the same sample is determined by the relaxation time discussed above. In particular, after the excitation signal has been removed, it takes approximately 3 times the relaxation time for the protons to return to their original aligned state in the static magnetic field, at which point a further burst of excitation current can be applied.

Separate measurements could be obtained either by using a number of different RF coils spatially separated along the Z-direction. Alternatively, the conveyor belt could be stopped each time a vial reaches the interrogation area and multiple measurements made.

Multiple measurements of the same sample may also be possible if the interrogation zone of the magnet and RF coil is large enough to allow multiple measurements to be taken considering the speed of the conveyor belt. In such an embodiment, the accuracy of the system will depend upon the homogeneity of the RF coil and the magnetic field within the interrogation zone as well as on the system signal to noise and the RF coil's fill factor. If the field patterns of the magnet and RF coil are known in advance, then this knowledge can be used to make corrections on the different measurement signals. Also, additional X, Y and Z coils (known in the art as shims) may also be provided to improve the homogeneity of the static magnetic field.

In one embodiment, a single vial is located within the RF coil 15 interrogation zone at any one time. FIG. 1a diagrammatically illustrates another embodiment in which the components of a check weighing station 3 allow multiple vials to be located within the RF coil 15 interrogation zone at the same time and which allow a mass measurement to be made of the sample within each vial individually. To achieve this, in such embodiment, in addition to the static magnet 13 and the RF coil 15, a separate pair of coils 71 and 73 are located either side of the conveyor belt 7, which operate to provide a magnetic field gradient across the conveyor belt 7. As a result of this gradient, the static magnetic field experienced by each of the glass vials will be different and thus the Larmor frequency of the sample in each of the three vials in the interrogation zone will be different. Consequently, each vial can be interrogated separately by applying three different narrow band RF pulses at the appropriate Larmor frequency.

Alternatively, a broad band RF pulse could be applied over the interrogation zone and the resulting MR signals from the samples can be resolved by taking the Fourier transform of the received signal after the excitation pulse has ended, as is standard practice in MR imaging.

Figure 1B:
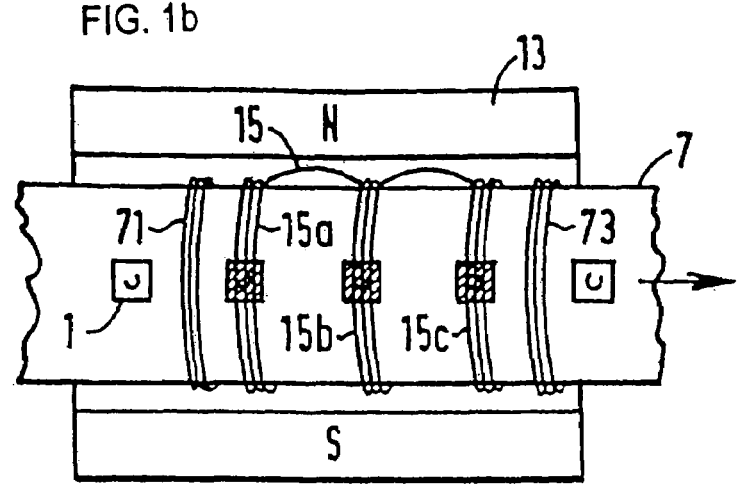
FIG. 1b diagrammatically illustrates an alternative check weighing station.

With reference to FIG. 1a, the gradient coils are arranged to apply a gradient in the same direction as the static magnetic field which is generated by the magnet 13. As is well known in the art of magnetic resonance imaging, gradient coils can be arranged to provide magnetic field gradients in one or more of the X, Y or Z axes so that the entire volume of the interrogation zone can be spatially resolved. FIG. 1b illustrates an embodiment where the two gradient coils 71 and 73 are provided at opposite ends of the RF coil's interrogation zone. In this embodiment, the RF coil 15 comprises three separate portions 15a, 15b and 15c. As those skilled in the art will appreciate, by applying a magnetic field gradient along the length of the conveyor belt 7 through the interrogation zone, each of the samples can be interrogated separately or simultaneously in the same way as in the embodiment described with reference to FIG. 1a. B refers to the magnetic field strength of the static magnetic field generated by magnet 13. As described in reference to FIGS. 1a, 1b and 1c, N and S refer to the north and south direction of the magnetic field respectively.

In the embodiments described with reference to FIGS. 1a and 1b, a plurality of samples were located within the interrogation zone and either interrogated separately or simultaneously. In these embodiments, since each of these samples will experience a slightly different magnetic field and will be in a different position relative to the RF coil, separate calibration data can be used for each of the sensing positions in order to try to reduce errors caused by inhomogeneities in the static magnetic field or in the RF coil.

Figure 1C:
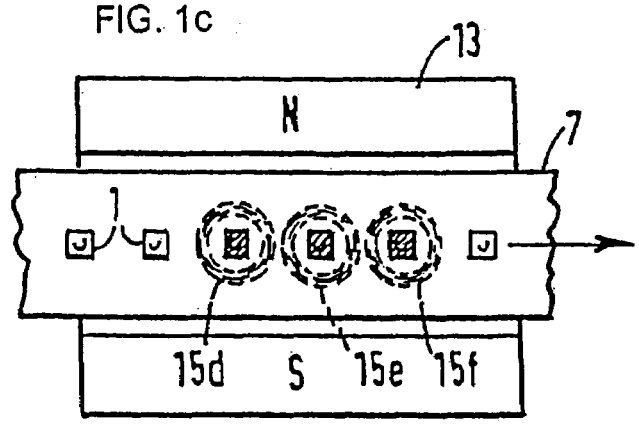
FIG. 1c illustrates a further check weighing station.

In the above embodiments, the RF coil generated a magnetic field in the Z-direction along the direction of movement of the conveyor belt 7. The RF coil can be located at any angle relative to the DC magnetic field, provided the field which it generates is relatively homogenous over the sample being tested and provided it comprises a component which is orthogonal to the static magnetic field. FIG. 1c diagrammatically illustrates an embodiment where three separate RF coils 15d, 15e and 15f are provided under the conveyor belt 7, each of which is operable to generate an AC magnetic field in the Y-direction. This embodiment allows the samples in three vials to be tested simultaneously. It also allows the system to interrogate the sample in each vial three times, once by each of the RF coils.

Figure 1D:
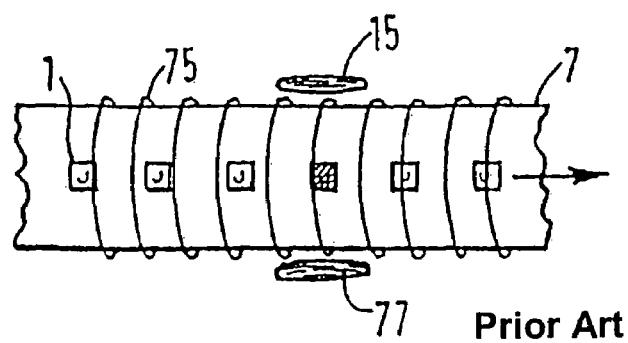
FIG. 1d illustrates another check weighing station.

In the above embodiments, a permanent magnet was used to generate the static magnetic field. As those skilled in the art will appreciate, electromagnets, current carrying coils or superconducting magnets could be used in place of the permanent magnet to generate the necessary DC magnetic field. Additionally, in the above embodiments, the DC magnetic field was applied across the conveyor belt in the X-direction. As those skilled in the art will appreciate, the DC magnetic field can be applied through the sample in any direction. For example, the north and south pole of the magnet may be placed above and below the conveyor with the RF coil being, for example, in the same orientation as in the first embodiment. FIG. 1d shows yet another embodiment in which a solenoid coil 75 is wound along a length of the conveyor belt 7 for generating the static magnetic field along the length of the conveyor belt 7, i.e. in the Z-direction. In this embodiment, the RF coil 15 is provided at one side of the conveyor 7 and a separate detector coil 77 is provided at the opposite side of the conveyor 7.

Figure 1E:
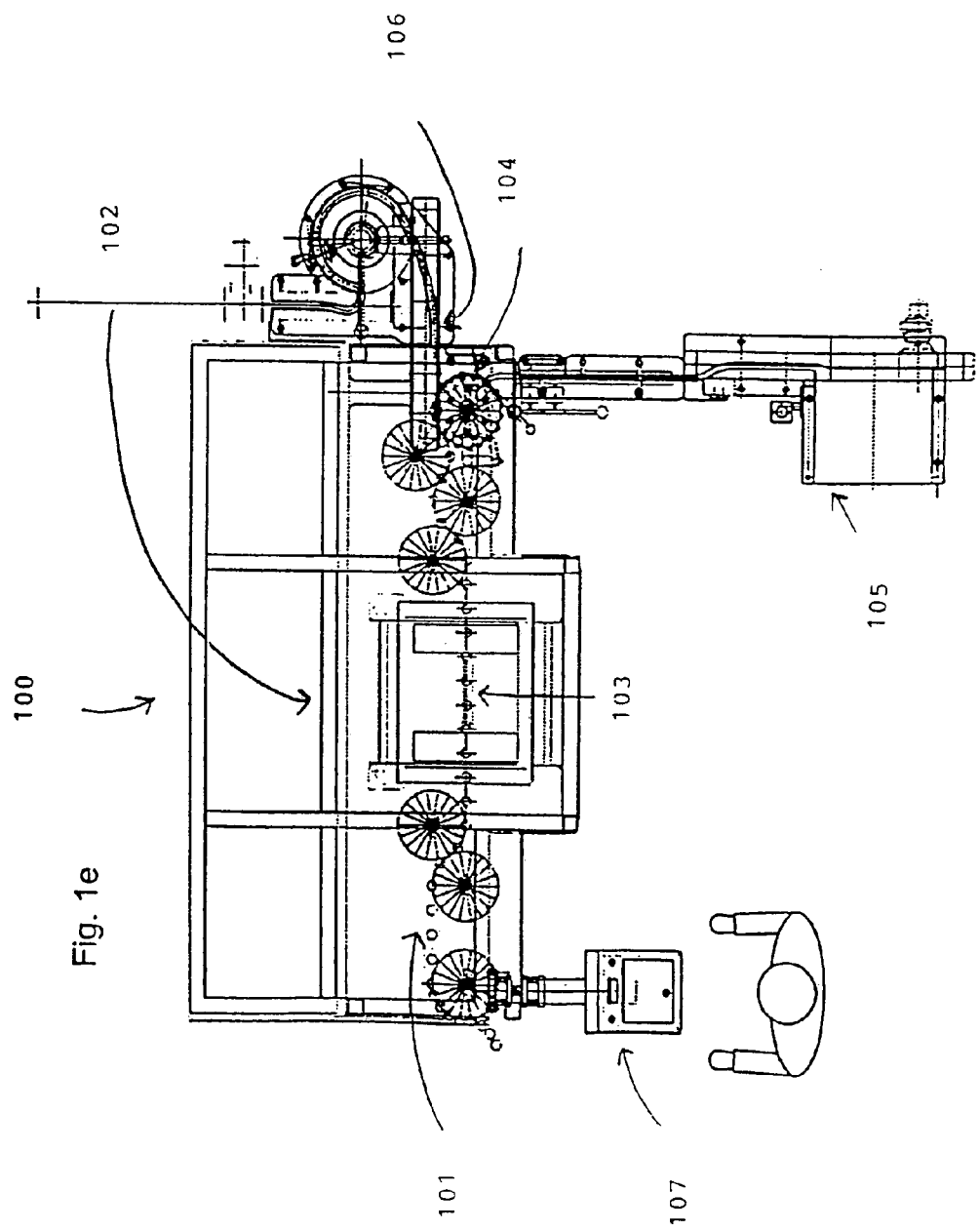
FIG. 1e is a schematic plan view of a production line with an NMR check weighing station.

FIG. 1e shows a schematic plan view of a production line with an NMR check weighing station. Generally, the check weighing station 100 includes an in-feed section 101 comprising a conveyor belt or other transport mechanism, the check weighing section 102 containing the magnet, RF antenna and in part defining the interrogation zone 103, a reject section 104 leading to a reject buffer 105, and an out-feed section 106. The check weighing station may contain an operator panel 107.

There are other configurations which will allow a measurement of the mass of the sample to be obtained.

Detection of Ferrous Particles in an NMR Measuring System

In a system using NMR techniques to determine the mass of the contents of containers on a continuous basis, such as by the use of Free Induction Decay (FID), the measurement is nondestructive and measurement taking is fast enough to enable 100% protocolling. Further, the system is not influenced by airflows of the surrounding environment. A disadvantage of the system, however, is its sensitivity for magnetizable (such as ferrous) particles. Those particles might come loose from container platforms due to abrasive effects. The particles are carried by the containers, and finally deposit on the transport belt that moves the containers through the system. The NMR measuring system is responsive to these deposits by reduction of the signal amplitude at the moment of probing the signal, generating effectively lower mass readings, and therefore erroneous results. There is currently no direct measurement available that determines the level and rate of this pollution.

A method is provided to determine independently the degradation of the NMR measuring system due to the accumulation of ferrous particles. One embodiment includes a method for the determination of ferrous particles inside packages or containers without destructive testing and without disrupting the movement of the production line.

Ferrous particles disrupt the homogeneity of a magnetic field. The consequence is that the FID (Free Induction Decay) of the pulsed NMR measurement is steeper than it would be in the perfectly homogeneous case. By applying a specific spin-echo experiment (measurement) it is possible to determine the 'true' decay. Comparing the original decay with the 'true' decay shows that the more particles are included in the volume, the more prominent the differences in decay are. After calibration with known samples, this method can be used to measure the content of ferrous particles.

The same method can also be applied to determine the quality of the conveyor system. It is possible that over time, metal (ferrous) particles adhere to the belt. Above a certain level, the decay is too fast and actually disturbs the quality of the weight measurement. Using the spin-echo sequence regularly allows the system to perform a self-check, and to issue an alarm when cleaning of the system is required.

While performing continuous tests over long periods we found that the standard deviation based on the whole set of measurements was growing. In other words, the accuracy of the weight measurements degraded. During these continuous tests, vials are placed in specific positions (pockets). When keeping track of the specific positions where the measured vials were placed, we found a correlation between the specific position and signal amplitude. We discovered that some of the pockets contained more magnetic particles than others. Also, when doing specific spin-echo experiments, we could conclude that this method of determination of magnet field homogeneity was correlated to the amount of ferrous material present.

When a 90° excitation pulse is applied to a magnetized sample, the nuclei of hydrogen respond by emitting a decaying signal of the same frequency as the excitation signal. This is called the Free Induction Decay (FID). This decay has several origins, including: the fact that the resulting magnetic moment gets realigned again with the main stationary field, and the fact that the precessing magnetic moments of the contributing nuclei get out of phase.

The dephasing of the magnetic moments themselves is largely caused by the homogeneity of the stationary magnetic field. Especially the ferrous particles mentioned above are a cause for this. Although immediately after the excitation pulse the signal amplitude is the same in both clean and contamination cases, it is not possible to get a measurement reading at that time due to settling times of filters and other electronic hardware. The fast decay will therefore always result in a smaller amplitude as compared to the original (clean) situation.

The FID is determined by a couple of factors, of which the homogeneity of the main magnet field and the spin-spin relaxation (T2) are the most prominent. The amplitude of the 'echo' in the spin-echo experiment relates to the 'true' FID related to the T2. Comparing the echo amplitude with the original FID provides information about the homogeneity of the main magnet field. This homogeneity is largely deteriorated by ferrous particles close to the product. Therefore this abovementioned comparison gives information about the amount of ferrous particles. This comparison can contain any possible mathematical technique using simple ratios or integrating steps.

In MRI technology, it is known that when applying special sequences of pulses, it is possible to determine specific aspects of the substances under consideration. One such sequence is known under the name Hahn's sequence or Spin-Echo sequence. The essence is that some time after the 90° pulse (spin) another pulse is applied, that of the 180° degree pulse (echo). The consequence of the latter pulse is that the actual amplitude of the decaying signal, without the influence of the magnetic inhomogeneities is probed. Since this signal is essentially weaker than the FID measurements taken earlier in the decay, this probing response cannot be used directly to measure the mass. The ratio between the measurement directly from the FID and the reading from the echo is a measure of the magnetic inhomogeneity, and therefore a measure of the contamination of the transport belt. With a clean belt, this ratio is higher than with a (ferrous-) contaminated belt. Using continuous sampling of this ratio, combined with useful filtering techniques, the status of the belt is continuously assessed as well.

This technique is demonstrated graphically in FIG. 3, wherein S1/E is a larger quantity than S2/E. As shown in the graph of FIG. 3, amplitude is shown at a time after the 90° pulse 110, at the measurement time 111, and at the echo signal time 112, where the clean signal 113 is S1, the "contaminated" signal 114 is S2, and the echo signal 115 is E. In the demonstration system used to make continuous measurements, the vial speed was varied between 200 and 570 vials per minute. The method as such, however, is not velocity dependent. The system can be adapted such that when the ratio falls below a predetermined value, an alarm will be issued indicating that the belt needs to be cleaned.

It has heretofore been unknown to use this spin-echo NMR technique to determine field homogeneity, to determine the amount of ferrous particles, or to monitor the quality of an NMR check weighing function.

The same method can be applied for quantitative detection of ferrous particles in other substances. In a more general case, metal particles as such may not directly influence the magnet field, but would introduce effects on the detection of the FID. This might be detected by applying pulse sequences other than spin-echo that are useful in other fields of NMR.

Continuous Adjustment of NMR Check Weighing System

In a system where NMR (or MRI) technology is used to determine the mass of the contents of containers on a continuous basis, material is transported into a magnetic field to be magnetized. A coil structure is used to emit electromagnetic radiation that excites the material. The same coil receives the subsequent decay signal, called Free Induction Decay (FID). In one embodiment, the system includes a permanent magnet creating a magnetic field of roughly 0.17 T in the center of the volume. Between the poles of the magnet, the coil structure is fitted. This coil acts as a sender and receiver of electromagnetic radiation. The coil structure design may be specially adapted to minimize airflow disturbance.

The NMR measurement is nondestructive and measurement taking is fast enough to enable 100% protocolling. Further, the system is not influenced by airflows of the surrounding environment. However, due to electronic drift effects, temperature variations and other effects, it is conceivable that the signal amplitude may drift as well. To prevent this a periodic verification with a standard is necessary.

Many conditions can give rise to detuning and drift of the system. Temperature, of both or either, of the magnet and the electronics could be the cause. There are many sources that may cause drift in the resulting signals. It is therefore necessary to regularly verify if the complete system is still well tuned. To stop production and run a 'golden sample' (control sample) causes disruption, but also is very complicated when the whole system is inside an isolator set-up. Further, such a practice is more difficult to validate and requires collecting a lot of statistical data.

When applying NMR techniques for weighing substances, a regular standardization step is necessary to compensate for many sources of drift. In traditional measurement procedures this is done by regularly presenting known weights to the weighing scale, and adjusting accordingly.

Certain embodiments of the method are directed to avoiding this regular standardization step, by fitting a so-called 'golden sample' inside the measurement system, at least semi-permanently. There are various ways to determine the right sample.

1. Choose the sample such that the response is in a frequency band different from the one from the product. This does not disturb the measurement of the product.

2. Choose the sample such that the decay is much faster than for the product. In that way the normal measurements will not be disturbed.

3. Choose the sample to behave exactly as the product, or choose the product itself. The advantage is that any correction based upon this sample is exactly the one needed for the product.

When integrating a specific sample of constant stability with the coil assembly, a reference signal can be obtained whenever needed. The constant stability sample can be one of the following.

1. A sample of a similar constitution as the product that needs to be measured. The consequence is that not only a reference can be obtained by determining a FID with just empty vials, but also that it is possible to actually measure containers that are empty. Without this reference, it is not possible to determine fills that are close to zero, due to noise effects.

2. A sample of such a constitution that the time to pre-magnetize is short (short T1). This allows for obtaining many reference signals in a short period of time without saturation effects.

3. A sample of such a constitution that the decay signal is very fast. In this way the normal measurements are undisturbed, because the sample decay is over when the measurement of the product is done.

The permanent compensation of potential drifts in the NMR measuring system is a major improvement of the functionality of the system, and additionally provides support for validation processes. Further, it facilitates the application of the NMR measuring system in isolators, useful in high purity systems.

Figure 4A:
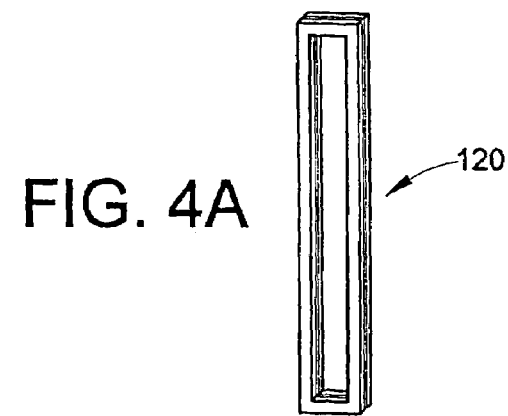
FIG. 4a, is a schematic diagram of the NMR transmit/receive probe wiring circuit.
Figure 4B:
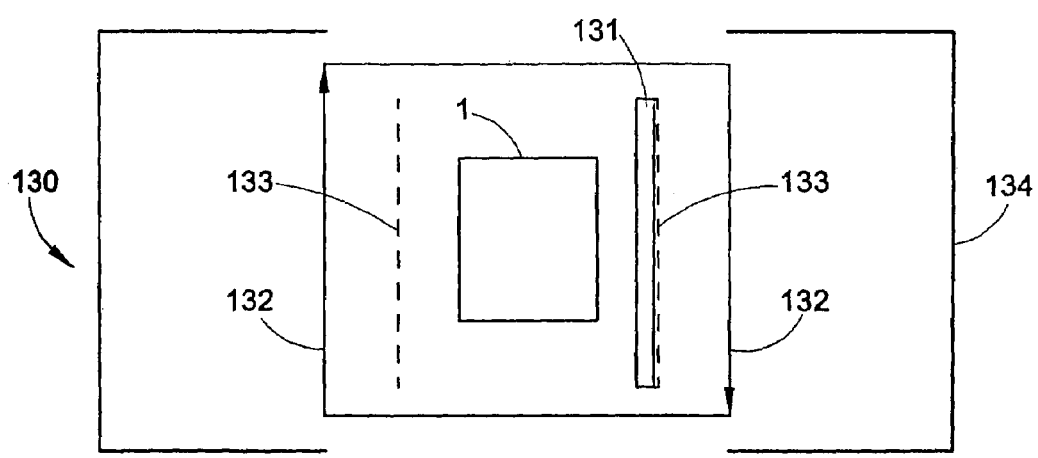
FIG. 4b is a schematic diagram of one embodiment inserting a stationary sample in the system.
Figure 4C:
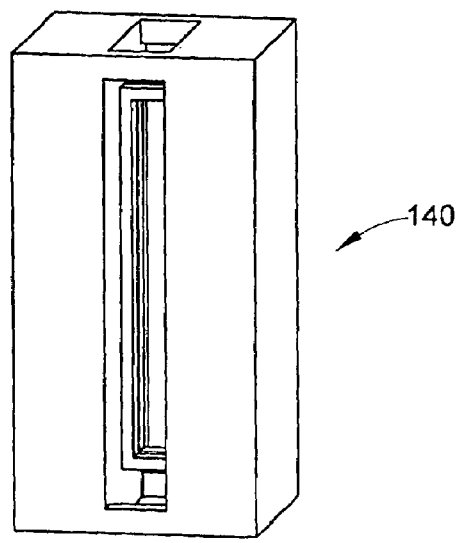
FIG. 4c is a schematic diagram of the NMR transmit/receive probe impression.

FIGS. 4a, 4b and 4c are schematic diagrams of the NMR transmit/receive probe and one embodiment inserting a stationary sample in the system.

FIG. 4a shows a schematic of the electrical wiring circuit 120 of the transmit/receive probe. The wiring is such that when an alternating current is induced a varying magnetic field is created in a direction perpendicular to the main magnetic field and in the direction of the transport mechanism. FIG. 4b shows that inside the transmit/receive coil 130, a stationary sample 131 is positioned. The transmit/receive coil 130 may comprise RF conductor 132 and optionally a Faraday cage 133 at least partially enclosed within cladding 134. A glass vial 1 is shown in the center of the outside of the transmit/receiver coil 130. FIG. 4c shows one embodiment of a layout of the transmit/receive coil 140.

Determining the Presence of Mercury in TL Light Sources

One of the production steps in TL light source production is the injection of a small amount of Mercury. Currently there is no method to determine non-destructively on a 100% check basis, the actual presence of this metal. NMR technology is highly sensitive to the presence of metals in the measurement volume (or interrogation zone), and therefore the distortion of any NMR signal present can be used as a means to verify the presence of this metal, or any other metal.

The NMR equipment includes a permanent magnet having a bore-size that allows a transportation means for the products that are measured to pass through an interrogation zone. Inside the magnet, a specific probe acts as a radio-frequency electromagnetic emitter/receiver that both excites the product material and receives the response. The probe construction is such that there is maximum allowance for transportation means to carry the products through the system. It is important to discriminate between products that do give rise to NMR signals and those that do not, such as glass, polyvinyl chloride (PVC), and polytertrafluoroethylene (PTFE).

According to this embodiment, the measurement probe will be equipped with a stationary sample of a piece of material that generates a stable NMR signal. The presence of a very minimal amount of metal particles inside the measurement volume will cause a severe degradation of the NMR signal amplitude. The amount of distortion can be measured and will serve to determine the actual amount of mercury present in the product passing through the interrogation zone.

In one embodiment the method involves implementation of a stationary sample inside of the magnet/antenna as discussed in further detail above. Further, the embodiment may include transport means adapted for moving the light sources in and out of the system.

When a product containing hydrogen protons is brought into a magnetic field, the associated magnetic moments are aligned to the external magnetic field lines. The alignment is not perfect; the vectors actually precess around the field lines. The precession frequency, the Larmor frequency, is linearly proportional to the external field strength and is therefore known. When applying a second magnetic field perpendicular to the external field with a frequency equal to the Larmor frequency, the precession starts to increase until the rotation is perpendicular to the original external field. When the transmit pulse is switched off, the magnetic moments return to the original situation while emitting a signal with the Larmor frequency. This decaying signal can be detected with the same antenna as the signal has been emitted originally, just by switching the electronic circuit by known means. When a substance is placed permanently inside the antenna, there will be a constant detection of the decay signals. Any additional metal (including but not limited to mercury) alone or in a product inside the antenna, will lead to a decrease of the amplitude of the decay signal, as NMR is highly sensitive to the influence of metals. Preliminary experiments with metal particles in oil samples showed that in some cases, a few micrograms of metal led to 30% reduction of the signal.

Determining Contamination of Metal Particles on a Non-Destructive Basis

The method is applicable for other situations where metals need to be detected in a non-destructive, non-contact way with high precision.

There are a vast number of products of which the quality depends on the total absence of metallic particles. NMR is highly sensitive to the presence of metallic particles in its measuring volume, and can therefore be applied to their detection. By way of example but not limitation, it can be employed for detection of metal particles in medicines.

Although the amplitude of the Free Induction Decay (FID) signal is linearly proportional to the amount of product, the shape of the FID is also dependent on some external conditions. Local magnetic field inhomogeneity may cause the FID to decline much faster. Ferrous particles cause local inhomogeneity and decrease the FID and the detected signal. The influence is related to the size of those particles, since the influence is related to interference with the NMR probe antenna.

It is known to apply visual inspection to check the contamination level of freeze-dried product. This method cannot discriminate the nature of the contamination, nor can it determine the contamination in the interior of the freeze dried cake. NMR measurements were applied to a number of visually determined contaminated product samples and a number of clean samples to determine the FID signals of the various samples.

Although the signal to noise ratio can be improved by focusing the NMR probe on the cake volume itself and by applying a higher magnet field, the NMR system was able to discriminate between the contaminated and clean samples by detecting an FID signal difference on the order of 20%. Although the experimental system did not discriminate between loss of signal due to metal particles and a low level of content, it is unlikely that a signal difference of 20% would be due to a difference in content weight of 20%. The system is therefore useful in indicating metal contamination of product samples, even if contamination is present in the interior of the freeze-dried cake, as the resulting signal for the contaminated samples were lower than expected.

As discussed above, the NMR apparatus includes a permanent magnet with a bore-size that allows a transportation means for the products that are measured to pass through an interrogation zone. In one embodiment, a specific probe may act inside the magnet as a radio-frequency electromagnetic emitter/receiver that both excites the product material and receives the response. The probe construction is such that there is maximum allowance for transportation mechanisms to carry products through the system. In one embodiment, the measurement probe will be equipped with a stationary sample, a piece of material that generates a stable NMR signal. The presence of a very minimal amount of metal particles inside the measurement volume will cause a severe degradation of the NMR signal amplitude.

In another embodiment, such as for products that do give rise to NMR signals, e.g. tissues and fluids, there is no need for insertion of a specific stable sample inside the measurement probe. The presence of small amounts of metal particles will cause the same type of signal distortion as the situation where a stable sample is at least semi-permanently disposed inside the interrogation zone.

In the application of NMR techniques to determine characteristics of the contents of containers, such as vials, in a non-stationary manner, prior to the sample being in the measurement position the sample is moving through the magnetic field and is therefore being pre-magnetised (or pre-polarised). At the measurement position, the sample may be excited with an excitation pulse, for example a 90° pulse. This pulse causes the spins of the protons to precess in a plane, perpendicular to the main magnetic field. The relaxation process is dominated by dephasing of the spin precessions of the individual protons, and this free induction decay (FID) signal is measured. The amplitude of this signal is linearly proportional to the amount of protons in the sample, and therefore a sample calibration allows the method to be used as a measurement method, such as for weighing.

The process of polarization is a process with a typical time-constant, the T1 (spin-lattice constant). Generally NMR measurements can be taken when the pre-magnetization is complete. This stage is reached when taking approximately 5 times T1 as a magnetization period. For many pharmaceutical products, the T1 is of the order of 1 second. For completely magnetised NMR measurements, a pre-magnetization step of 5 seconds would be necessary.

In embodiments in which the method is applied to fast moving samples, the measurement is applied to incompletely magnetised samples and this measurement is accurate enough if the history (in terms of exposure to the magnetisation field) of every subsequent sample is identical, for example: the T1 influencing factors are known (via specific calibration) and can be incorporated into the measurement calculations (for example, temperature), and the speed of every subsequent sample does not vary, or is accurately known and can be compensated for.

Figure 5:
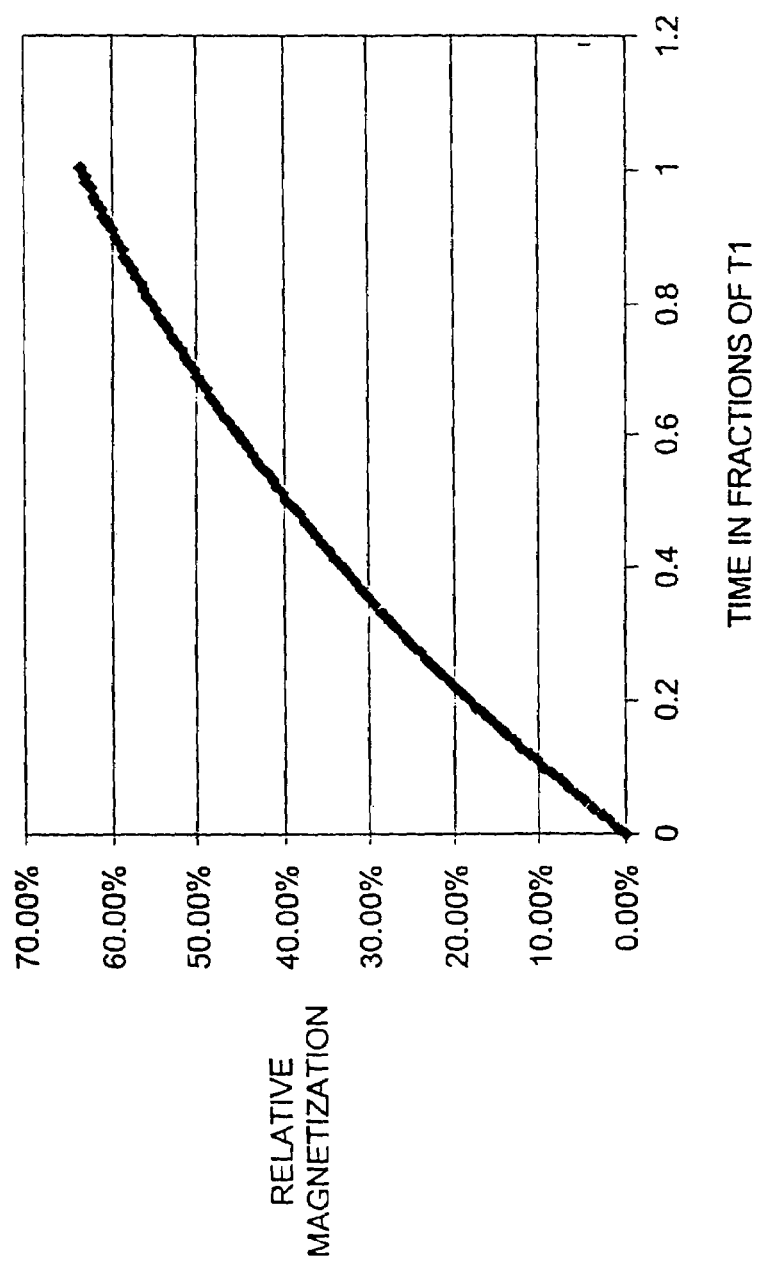
FIG. 5 is a graph showing a polarisation curve comparing relative magnetization to time in fractions of T1.

The graph of FIG. 5 shows a magnetisation curve and the consequence of having typically only half of a T1 available for magnetisation, yielding only 39% of magnetisation.

Although the invention has been described in detail through the above detailed description and the preceding examples, these examples are for the purpose of illustration only and it is understood that variations and modifications can be made by one skilled in the art without departing from the spirit and the scope of the invention. It should be understood that the embodiments described above are not only in the alternative, but can be combined.

We claim:

1. A nuclear magnetic resonance method configured for use in a magnetic resonance measuring system having at lest least one magnetic field in order to determine the mass of non-continuous and discrete samples in a production line, the nuclear magnetic resonance method providing compensation of drift in the nuclear magnetic resonance measuring system, comprising:
   a) applying a first magnetic field in a first direction in an interrogation zone in order to create a net magnetisation within a first sample having unknown mass and at least one other non-continuous and discrete second sample of known mass located within the interrogation zone;
   b) applying an alternating magnetic field in a second direction in the interrogation zone in order to temporarily change the net magnetisation of the first sample and the second sample located within the interrogation zone;
   c) monitoring energy emitted by the first sample while the first sample is in the interrogation zone as the net magnetisation of the first sample returns to its original state and generating a first output signal having a characteristic which is proportional to the energy emitted by the first sample;
   d) monitoring energy emitted by the second sample within the interrogation zone as the net magnetization of the second sample returns to its original state and generating a second output signal having a characteristic which is proportional to the energy emitted by the second sample and which corresponds to the characteristic of the first output signal;
   e) comparing the first output signal characteristic with corresponding characteristics of the first output signal and the second output signal in order to determine the unknown mass of the first sample;
   f) maintaining a constant stability third sample within an access of the interrogation zone during steps a) through d);
   g) at least periodically performing measurements of the mass of the constant stability third sample by applying the first magnetic field in the first direction in the interrogation zone in order to create a net magnetisation within the constant stability third sample located within the interrogation zone, applying the alternating magnetic field in the second direction in the interrogation zone in order to temporarily change the net magnetization of the constant stability third sample located within the interrogation zone, monitoring energy emitted by the constant stability third sample as the net magnetization of the constant stability third sample returns to its original state and generating a third output signal having a characteristic which is proportional to the energy emitted by the constant stability third sample;
   h) comparing the periodically performed constant stability third sample mass measurements in order to determine, over time, an amount of drift in the magnetic resonance measuring system; and
   i) when appropriate adjusting the first sample mass and the second sample mass measurement values in order to compensate for the amount of drift in the magnetic resonance measuring system.

2. The method of claim 1 wherein the first output signal, the second output signal and the third output signal are each in a frequency band, and the third output signal is in a frequency band different from the frequency band of the first output signal and the second output signal.

3. The method of claim 1 wherein the first output signal, the second output signal and the third output signal each have a decay, and decay of the third output signal is faster than the decay of the first output signal and the second output signal.

4. The method of claim 1 wherein the constant stability third sample is adjusted in order to produce an adjusted third output signal which is the same as the output signal of the first sample and the output signal of the second signal.

5. The method of claim 1 wherein the constant stability third sample is a sample with standardized properties.

6. The method of claim 1 wherein the first sample output signal characteristic, the second sample output signal characteristic and the third sample output signal characteristic are each current amplitude.

7. The method of claim 1 wherein the monitoring of the first, second and constant stability third samples as well as the generating of the first, second and third output signals occurs before the net magnetization of the first, second and constant stability third samples reach a complete magnetization at T1.

* * * * *